United States Patent [19]

Hirbod

[11] 4,273,615

[45] Jun. 16, 1981

[54] OIL STIMULATION PROCESS

[76] Inventor: Farrokh Hirbod, 6424 Via Colinita, Rancho Palos Verdes, Calif. 90274

[21] Appl. No.: 925,576

[22] Filed: Jul. 17, 1978

[51] Int. Cl.³ .......................................... E21B 43/263
[52] U.S. Cl. ..................................... 176/39; 166/246; 166/247
[58] Field of Search ................... 176/39; 166/246, 247, 166/299; 585/240, 241

[56] References Cited

U.S. PATENT DOCUMENTS

| | | | |
|---|---|---|---|
| 3,105,014 | 9/1963 | Harrison | 166/246 X |
| 3,113,620 | 12/1963 | Hemminger . | |
| 3,233,670 | 2/1966 | Thompson et al. | 176/39 X |
| 3,659,649 | 5/1972 | Dunlap | 176/39 X |
| 3,707,188 | 12/1972 | Heckman | 166/247 |
| 3,712,374 | 1/1973 | Terhune | 166/247 |
| 3,764,660 | 10/1973 | Krikorian | 176/39 X |
| 3,814,185 | 6/1974 | Boardman | 166/247 |
| 3,864,208 | 2/1975 | Van Huisen . | |
| 3,936,353 | 2/1976 | Chen | 585/240 X |
| 4,046,630 | 9/1977 | Coast et al. | 176/39 |

*Primary Examiner*—Peter A. Nelson

*Attorney, Agent, or Firm*—Nilsson, Robbins, Dalgarn

[57] ABSTRACT

A method of converting organic waste into useful petroleum products and for recovering previously unrecoverable residual oil in oil bearing geologic layers. An organic slurry containing obligatory anaerobes is first formed from garbage, sewage and the like to which may be added various catalysts such as iron or cobalt. The slurry is then pumped into a geological layer, which is preferably oil bearing, having a temperature of a magnitude which allows anaerobic digestion to continue. One or more explosive devices are positioned above the geological layer and below an explosion directing cap. After a period of anaerobic digestion, the explosive devices are detonated causing heat and pressure to be applied to the organic waste in the geological layer. The combination of heat and pressure cause various chemical reactions, including molecular restructuring, to occur which convert the organic waste into various petroleum products. The catalyst added to the organic slurry encourages certain physiochemical reactions to occur more prevalently thus allowing some control over the particular petroleum products which will result.

10 Claims, 3 Drawing Figures

OIL STIMULATION PROCESS

BACKGROUND OF THE INVENTION

The present invention relates to a method of producing petroleum and petroleum products from organic wastes and, in particular, a method for producing petroleum products by placing the organic waste in a permeable earth layer and subjecting the organic waste to high pressure and heat produced by the detonation of one or more explosive devices.

In nature, it is believed that gas and oil deposits are formed from organic materials which accumulate in layers in a given area. These organic deposits have not only decayed and decomposed to some degree but have slowly been buried as various forms of sedimentation occur. The progressive deepending of the layer of organic material plus geological upheavals cause the organic materials to be buried deep in the earth and subjected to enormous pressures as well as geothermal heat which eventually converts the organic materials to petroleum and petroleum related compounds. The present invention in effect duplicates this process in order to form petroleum compounds. However, the present invention performs this process in as short a time as several weeks while the natural process will normally occur over millions of years.

Various methods are known for producing methane gas from organic waste such as sewage and garbage. Specifically, in U.S. Pat. No. 4,057,401, filed Sept. 3, 1976 by Boblitz, an improved method of producing methane gas via bacterial action is described in which the production is facilitated by heating large quantities of organic waste material to promote the bacterial decomposition. However, in that patent, large quantities of complex equipment, including digester tanks, air tight enclosures surrounding the tanks, solar heaters, various conduits and various pumping apparatus, are required. By contrast, in the present invention, all that is required is a simple pump to pump the organic slurry into a permeable earth strata preferably having a temperature of about 100° F. although a temperature of between 50° and 150° F. is also acceptable.

In another U.S. Pat. No. 3,640,846, filed Apr. 29, 1969, by Johnson, another method of producing methane from sewage solids is described in which the addition of coal substantially increases the production of methane by anaerobic digestion process. However, in that patent, there is no suggestion that production of methane by anaerobic digestion can be done in an earth strata or enhanced by the utilization of residual quantitites of oil in the earth strata in place of coal. Although such a result is not certain, it is believed that the residual oil contained in oil bearing geological formations will also promote the production of methane from an organic slurry comprised of sewage and pulverized garbage in the same manner that coal promotes the process described in the cited patent. In any event, the production of methane gas by anaerobic digestion comprises just one step in the present invention which includes a method of producing other petroleum components as well.

In another U.S. Pat. No. 3,606,999, filed Aug. 4, 1967, by Lawless, a method and apparatus for carrying out a chemical or physical process is disclosed in which it is necessary to apply high pressure to the various materials in order for the chemical reaction to occur. In particular, it provides for the oxidation of continuously flowing waste streams, such as sewage, by subjecting those waste streams to high pressure at suitable temperatures to induce various organic chemical reactions to produce organic compounds. In this patent, however, a deep well is drilled into the earth and filled with water. The head of water provides the necessary pressure. The materials to be reacted with each other are then pumped to the bottom of the well and subjected to the high pressures provided by the head of water. If heat is required, then artificial means must generally be provided to generate the heat.

By contrast, the present invention does not require the complex apparatus which the above patent requires. In addition, the above-cited patent does not provide for anaerobic digestion of any sort. Consequently, all the cited patent does is provide a high pressure zone into which various chemicals may be injected to induce chemical reactions which require high pressures.

In still another U.S. Pat. No. 3,864,208, filed Apr. 11, 1972, by Van Huisen, a process is disclosed for the destructive distillation of organic waste to produce gas and oil products. In this technique, an explosion is set off deep under the earth in a geological formation having a geothermal temperature of at least 300° F. The explosion creates a cavity containing a large quantity of rubble having a high ambient temperature. Organic slurry is then pumped into the hot rubble. As the organic slurry percolates up through the hot rock, it is destructively distilled forming a layer of oil on top of the water containing the organic slurry.

By contrast, the present invention pumps the organic slurry into the earth prior to setting off the explosion not after. In addition, the cited patent nowhere suggests or discloses the use of a depleted or oil bearing geological layer as is preferred in the present invention, but rather requires an active geothermal geological layer. It will, of course, be appreciated that in such a hot geothermal layer, the anaerobic digestion of the present invention will not be possible because such digestion cannot occur above about 150° F. Furthermore, the present invention utilizes an explosion to create heat and pressure which are immediately applied against the organic slurry to change the organic slurry into petroleum and gas products. Finally, unlike the above-cited patent, the method of the present invention is preferrably performed in an oil bearing geological layer containing otherwise non-recoverable petroleum. Thus, another advantage of the present invention over the prior art is that as a side product the heat created by the explosion of the present invention causes the otherwise unrecoverable oil deposits to be heated and made more viscous and thus more readily recoverable. Of course fields which have already been surveyed and found to be possible oil bearing areas are also acceptable geologically even though oil was not subsequently found. Use of such field and the existant geological data can greatly reduce the cost of practicing the present invention.

In this regard, U.S. Pat. No. 3,113,620, filed July 6, 1959, by Hemminger, discloses a particular method of generating heat in a depleted oil well to make oil therein which would otherwise be non-recoverable more viscous and, thus, recoverable. However, the present invention does not incorporate or require the elaborate process in that invention and indeed the present invention has as its primary objective the creation of oil rather than the recovery of previously non-recoverable oil.

Finally, it will be appreciated that in one alterative of the present invention, various elements or compounds such as iron or cobalt may be added to the organic slurry. When the explosive device is detonated these elements act as catalysts to promote the production of certain petroleum compounds over others. Thus, a certain amount of control over the type and quantity of various petroleum compounds is afforded.

SUMMARY OF THE INVENTION

The present invention comprises a process of converting organic waste which may include garbage or sewage into petroleum compounds. Initially, an organic slurry is formed comprising organic particles suspended in a liquid. The organic slurry is then pumped into an earth strata which preferably has an ambient temperature of between about 50° and 150° F. so that anaerobic digestion of the slurry is allowed to continue after the slurry is in the ground. After a period of time at least one explosive device is provided in a region above the earth strata and detonated for providing heat and pressure on the organic slurry. Petroleum compounds are then produced through various chemical processes and molecular exchange, i.e. changes in the molecular structure, which are induced by the high pressure and heat.

In another optional step, various catalysts such as iron or cobalt may be added to the organic slurry either before or after pumping the slurry into the earth strata. The presence of catalysts promote certain chemical reactions over others during the petroleum generation process (either before or during the application of pressure and heat) thus permitting a degree of control over the nature and quantity of petroleum compounds ultimately produced.

In order to promote anaerobic digestion, the process may include the additional step of adding obligatory anaerobes to organic slurry either before or after the organic slurry is pumped into the earth strata. In addition, the sea water may be used to provide the liquid for the slurry particularly for the pulverized garbage. The sea water thus also adds certain organic matters to the organic slurry.

The step of providing at least one explosive device may comprise, for each of the explosive devices, the further step of providing a cap above the explosive device. The cap may be made of concrete and preferably has a size, shape and strength which will contain and direct the explosive force and heat against the organic slurry rather than allowing it to escape away from the organic slurry. The concrete layer may be formed by injection of liquid cement into the area above the explosive devices. Of course, a concrete cap will be unnecessary if the strata above the explosive is strong or hard enough to contain the explosive.

While the present invention may be practiced using conventional explosive devices, in the preferred embodiment, the explosive device will be nuclear. In addition, when a nuclear device is utilized, the device preferably is of a kind which generates low quantitites of residual radioactivity which, in any event, dissipates rapidly after the explosion occurs.

In positioning the explosive devices when more than one explosive device is utilized, it is preferable to arrange them in a grid pattern and then explode the devices simultaneously to provide a substantially uniform application of pressure and heat.

In the preferred method of the present invention, the earth strata contains carbonacious matter which may, for example, be residual oil such as that remaining in a depleted oil field. Furthermore, it is preferable that there be a relatively impermeable, hard earth strata below the earth strata into which the organic slurry is pumped to contain the pressure created by the explosion.

Finally, it is preferred that the organic slurry be substantially deoxygenated to promote organic chemical reaction without the possibility of oxidation reactions occuring. Deoxygenation may be promoted by the presence of hydrogen sulfide ($H_2S$) which reacts to absorb free oxygen. The hydrogen sulfide may either exist in the slurry already or may be added to the slurry.

BRIEF DESCRIPTION OF THE DRAWINGS

The invention will be better understood from the detailed description taken below in conjunction with the drawings wherein like reference characters refer to like parts throughout and in which.

DETAILED DESCRIPTION

Figure 1:
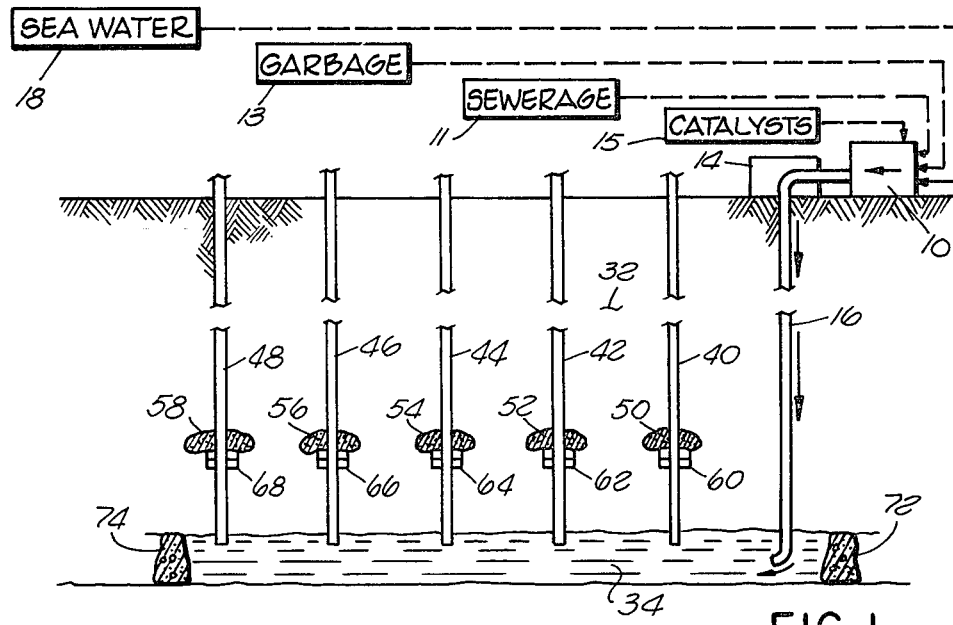
FIG. 1 is a schematic side view through the earth illustrative of the method of the present invention prior to detonation of the explosive devices.

The method of the present invention may be described in conjunction with the illustration of FIG. 1 in which a treatment plant 10 is provided for receiving sewage 11, garbage 13 and any other organic waste material for producing an organic slurry containing small particles of organic matter in suspension. In order to form the slurry, the treatment plant 10 may include grinders, pulverizers and any other equipment necessary to pulverize the organic materials into a flowable mass. If needed, additional liquification may be realized by combining or adding sea water 18 or other water to the garbage and sewage. In addition, the organic slurry may include sludge, which is a by-product of the activated sludge processing system. Finally in the preferred embodiment, the treatment plant provides deoxygenation so that aerobic bacterial action is inhibited and carbonaceous matter preserved. Such deoxygenation may be provided by the existing or added hydrogen sulfide ($H_2S$) or similar compound.

Various catalysts 15 may also be added to the slurry generated at the treatment plant. The catalysts are provided to promote certain chemical reactions and molecular structure reorganization over others to thereby allow some control over the nature and quantity of petroleum compounds ultimately formed by the process of the present invention.

The resultant organic slurry is next pumped by a pump 14 through a pipe 16 which extends into the ground, and into a geological layer 34 which is preferably an oil bearing sand layer. The slurry may be kept in a specified region of the earth strata by appropriately sealing such as with cement plugs illustrated by the reference numerals 72 and 74. These plugs may be formed by the injection of cement through appropriate wells (not shown.) Such an oil bearing sand layer may be the layer in a depleted oil field which still contains substantial amounts of non-recoverable oil. Of course, it will be appreciated that any geologic formation or layer containing organic materials such as oil or coal is acceptable in accordance with the present invention. Furthermore, the layer need not necessarily contain existing organic material although its existence is preferable.

The concentration of anaerobes, already in the slurry, may be increased by adding anaerobes to the organic slurry. Anaerobic digestion, which may begin prior to pumping the slurry into the geographical strata, continues to occur by the action of obligatory anaerobes. The actual process by which anaerobic digestion occurs and the requirements of that process are described in U.S. Pat. No. 4,057,401 which issued Nov. 8, 1977, by Boblitz.

As described in the above patent, one of the problems of producing methane gas via bacterial action is the heating of large quantities of material to promote that bacterial decomposition. Consequently, in the present invention, it is preferable that the earth strata 34 has an ambient temperature of about 95° to 100° F., although a wider temperature range of about 50° to 150° F. can be tolerated. By providing such a temperature range, anaerobic digestion of the organic slurry occurs for a predetermined period of time after the organic slurry is pumped into the earth strata. In addition, if the anaerobic digestion is allowed to occur in a carbonaceous or oil bearing sand layer, the production of methane gas will be promoted in a manner somewhat analogous to that disclosed in U.S. Pat. No. 3,640,846 which issued Feb. 8, 1972, by Johnson.

In general, if the earth strata 34 is in a depleted oil field, a number of abandoned oil wells will already be positioned in various locations. However, new wells may be drilled into the oil bearing sand layer or at least to a point somewhat above the oil bearing sand layer to supplement the existing wells and to provide the grid pattern of the explosive devices previously disclosed. Of course, use of existing wells whether bore hole, test holes or wells of a depleted oil field, greatly decreases costs since much of the existing equipment may be used. Also, areas without recoverable oil but in which geological survey information has been obtained are acceptable and even preferable in practicing the present invention. Use of such existing geological data can greatly reduce the cost of practicing the present invention since new studies will not be necessary.

For example, in FIG. 1, wells 40, 42, 44, 46 and 48 extend from the surface of the ground 30 through various strata of rock 32 into the earth strata 34 constituting an oil bearing sand layer. In accordance with the present invention, each of the wells is respectively provided with an explosive device 60, 62, 64, 66 and 68. The explosive devices may be either high yield conventional explosives or may be thermonuclear or nuclear bombs. Caps 50, 52, 54, 56 and 58 may respectively be formed above each of the explosive devices to concentrate and direct the explosion forces and heat and to prevent the escape of radiation when a nuclear device is used. This cap may be made of concrete and may be formed by first providing a cavity using a part of the method disclosed in U.S. Pat. No. 3,113,620 which issued Dec. 10, 1963, by Hemminger. Such a method would produce a cavity above the position where the explosive device was to be placed. The cavity could then be filled with liquid cement to form a cap above each of the explosive devices. Of course, providing such a cap is optional and need not be incorporated particularly if the earth strata above that into which the slurry is pumped is sufficiently strong to prevent radiation leakage and to concentrate the heat and pressure against the slurry.

In the preferred embodiment, each of the caps is generally conically shaped so that the explosive force of the explosive device will be directed downward against the organic slurry contained in the earth strata 34. Of course, the cap in practice will be irregular and only generally conical in shape. In one embodiment, the cap for a nuclear explosive is placed approximately 50 feet above the organic slurry in the earth strata. Of course, it will be appreciated that the larger the explosive device, the further away the cap must be positioned from the slurry containing earth strata while the smaller the explosive device, the closer the cap must be formed to the slurry containing earth strata to obtain optimum results.

In the preferred embodiment, the distance at which nuclear explosive devices are placed above the organic slurry is sufficient so that the cavity forced by the explosion does not extend into the earth strata containing the organic slurry. Thus, the organic slurry will be afforded some protection from residual radiation by the earth region between the slurry containing layer and the cavity forced by the explosion. This will be particularly true when the oil is withdrawn through the well 16.

Figure 2:
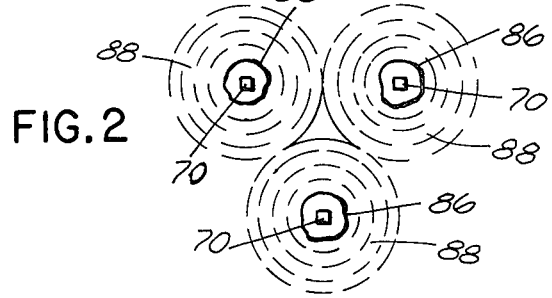
FIG. 2 is a top view illustrating the grid pattern of the explosive devices above an earth strata into which organic slurry has been pumped.

Referring now to FIG. 2, there is shown a top view of a plurality of explosive devices placed in a grid pattern above, for example, an abandoned oil field or a region of oil bearing sand into which has been pumped a quantity of organic slurry. The explosive devices 70 placed under the caps 86 may be exploded simultaneously or in sequence and preferably have overlapping explosive effect regions 88 so that the region effected by the explosive blast of one of the explosive devices 70 will overlap the regions effected by the explosive blasts of the adjacent explosive devices.

Figure 3:
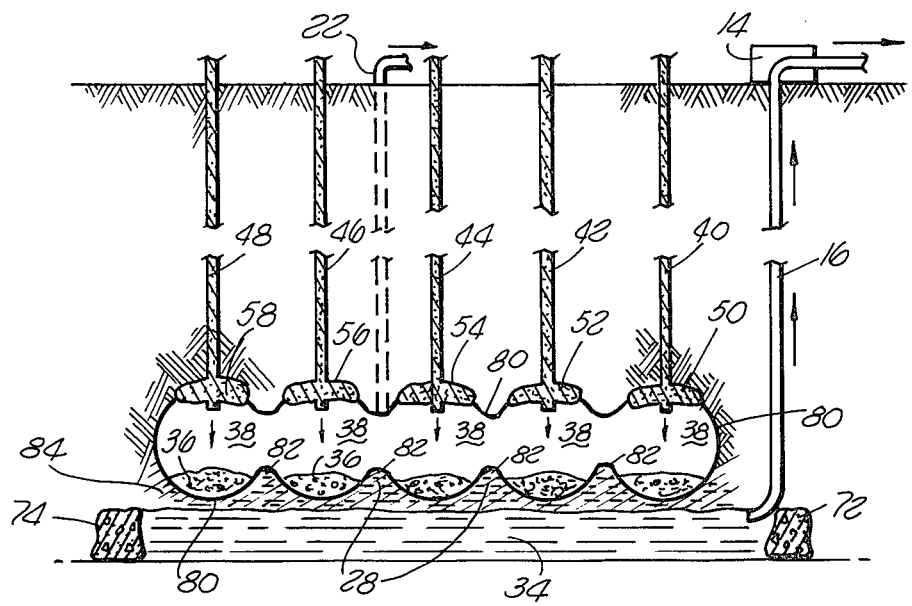
FIG. 3 is a side view illustrating the method of the present invention after the explosive devices have been detonated.

Referring now to FIG. 3, there is shown an arrangement in accordance with the method of the present invention after the explosive devices illustrated in FIGS. 1 and 2 have been exploded. Prior to exploding the explosive device, each of the wells 40, 42, 44, 46 and 48 is preferably filled with concrete to prevent any of the explosive effects from being dissipated through the respective wells regardless of whether a cap is used or not. When the explosive devices are detonated, heat and pressure is generated and is applied downward and may be assisted by the respective caps 50, 52, 54, 56 and 58 (when caps are in fact used) towards the organic slurry in the earth strata 34. Such heat and pressure cause the organic slurry, which has been previously subjected to anaerobic digestion for the production of methane gas, to be converted to petroleum compounds via various chemical reactions, and processes including molecular exchange reactions, as aided by any catalysts which may have been added to the slurry.

When a nuclear explosive device is used, a plurality of large cavities 38 will initially be formed below the respective caps 50 through 58. The cavities may be separated or may be joined depending on the initial arrangement of the nuclear explosive devices. Because of the high heat involved in a nuclear explosion, the rock previously in the interior of each cavity becomes molten and is forced out around the surface of each cavity. When the molten rock cools, a relatively impenetrable crust 80 will be formed on the top, bottom and sides of each cavity 38. Liquid and gas are thus largely prevented from entering the cavieties 38 with oil collecting in the less compacted regions 82 between the adjoining cavities. Alternatively, if cracks or other breaks in the bottom regions of the crust 80 exist, the oil and gas will enter the cavities 38. Of course, as disclosed in U.S. Pat. No. 3,864,208, a pile of rubble 36 may result in the bottom of each cavity through which residual organic slurry may undergo destructive distillation. However, the present invention is essentially unlike the invention of U.S. Pat. No. 3,864,208 in that the orgaic slurry is converted to petroleum compounds by the actual impact of the heat and pressure. One advantage of the present invention is that the resulting oil will be more readily protected from radiation contamination since the oil is kept outside the interior of the cavities by the impenetrable crust 80, at least for sufficient time to allow the radiation contamination to dissipate.

Because a substantial quantity of water will be contained in the oil bearing sand layer 34 and because the oil contained in that said layer plus the oil created by the heat and pressure on the organic slurry will be lighter than the water, the oil will float above the water through the compressed permeable rock layer 84 and accumulate in reservoirs at the peak locations 82 above the layer 84. This oil may be pumped out directly by drilling a new well 22 and pumping the oil out through that well. Alternatively, the well 16 may be utilized to withdraw oil utilizing the pumping apparatus 14.

The present invention provides a means for producing methane gas utilizing anaerobic digestive process prior to detonating the explosive devices and then utilizing various chemical reactions and molecular exchange reactions which occur under high pressure and heat to produce petroleum compounds.

Thus, there has been disclosed a novel method for producing petroleum compounds from organic waste by substantially duplicating the natural process in a relatively short period of time encompassing anywhere from several weeks to several years. In addition, the present invention, as a side benefit, allows a substantially greater quantity of previously unrecoverable oil in any oil bearing earth strata utilized, to be recovered by making the pre-existing oil more viscous due to the heating effect of the explosion, by the use of water in the slurry to wash the oil from the oil bearing sand, and finally, by providing conditions which promote the chemical reactions whose end products are more easily recovered.

Thus, there has been described a novel method for the recovery of previously unrecoverable oil plus the conversion of waste products into recoverable oil and oil products.

I claim:

1. A method of converting organic matter having a multiplicity of organic molecular structures to petroleum products by exploding an explosive device which forms an earth cavity comprising the steps of:

combining the organic matter with water to form an organic slurry;

pumping the organic slurry into a first earth strata having an ambient temperature less than about 150° F.;

allowing anaerobic digestion of the slurry in the first earth strata to occur;

providing at least one explosive device in a region above the first earth strata the distance between the explosive device and the first earth strata and the yield of the explosive device being selected so that the cavity formed upon ignition fo the explosive device does not penetrate the first earth strata; and igniting the explosive device for providing heat and pressure indirectly against the organic slurry after anaerobic digestion occurs for facilitating chemical and molecular alteration of the organic molecular structures of the organic slurry for producing petroleum compounds from the organic slurry.

2. The method of claim 1 comprising the additional step of adding obligatory anaerobes to the organic slurry for promoting anaerobic digestion in the first earth strata.

3. The method of claim 1 wherein the step of providing an organic slurry comprises the substep of deoxygenating the organic slurry for promoting anaerobic digestion.

4. The method of claim 1 wherein each explosive device is a nuclear explosive.

5. The method of claim 1 wherein each explosive device is a non-nuclear, conventional explosive.

6. The method of claim 4 or claim 5 wherein the step of providing at least one explosive device comprises, for each explosive device, the further step of providing a capping means above the explosive device for containing the explosion and directing the force and heat of the explosion toward the organic slurry in the first earth strata.

7. The method of claim 4 or claim 5 wherein a plurality of explosive devices are employed, the plurality of explosive devices being positioned in spaced relationship to each other in a generally horizontal grid pattern above the organic slurry whereby the heat and pressure generated by exploding the plurality of explosive devices are applied substantially uniformly against a predefined area of the first earth strata containing the organic slurry.

8. The method of claim 1 wherein the step of providing an organic slurry further comprises adding at least one nonorganic catalytic agent for promoting selected chemical reactions which yield selected petroleum compounds.

9. The method of claim 1 wherein the first earth strata into which the organic slurry is pumped is relatively permeable and is positioned above a second relatively impermeable earth strata for preventing the cavity from penetrating the first earth strata.

10. The method of claim 1 wherein the first earth strata contains residual amounts of carbonaceous compounds.

* * * * *